United States Patent [19]
Söring

[11] Patent Number: 5,626,560
[45] Date of Patent: May 6, 1997

[54] DIATHERMIC HAND-HELD INSTRUMENT WITH AN ENDOSCOPIC PROBE

[75] Inventor: Holger Söring, Quickborn, Germany

[73] Assignee: Soring Medizintechnik GmbH, Quickborn, Germany

[21] Appl. No.: 558,930

[22] Filed: Nov. 13, 1995

Related U.S. Application Data

[63] Continuation of Ser. No. 222,301, Apr. 4, 1994, abandoned.

[30] Foreign Application Priority Data

Apr. 13, 1993 [DE] Germany .......................... 93 05 428.9
May 12, 1993 [DE] Germany .......................... 93 07 183.3

[51] Int. Cl.⁶ .................................................. A61B 17/20
[52] U.S. Cl. ................................... 604/22; 606/37; 604/43
[58] Field of Search ............................ 604/20–22, 282, 604/43–45; 601/2; 600/158; 606/37, 40, 49, 50, 169, 39

[56] References Cited

U.S. PATENT DOCUMENTS

| | | | |
|---|---|---|---|
| 2,376,265 | 5/1945 | Meredith | 219/15 |
| 2,444,767 | 7/1948 | Cobean | 219/14 |
| 2,555,017 | 5/1951 | Tuthill | 219/14 |
| 2,612,584 | 9/1952 | Morrissey | 219/75 |
| 2,708,933 | 5/1955 | August | 128/303.14 |
| 2,797,306 | 6/1957 | Qualey | 219/75 |
| 2,828,747 | 4/1958 | August | 219/75 |
| 2,842,656 | 7/1958 | Neuvirth | 219/75 |
| 3,081,770 | 3/1963 | Hunter | 604/44 |
| 3,261,961 | 7/1966 | Spark | 219/75 |
| 3,529,128 | 9/1970 | Cruz, Jr. | 219/75 |
| 3,823,717 | 7/1974 | Pohlman et al. | 604/22 |
| 3,828,780 | 8/1974 | Morrison, Jr. | 604/20 |
| 4,040,426 | 8/1977 | Morrison, Jr. | 128/303.17 |
| 4,057,064 | 11/1977 | Morrison, Jr. et al. | 128/303.17 |
| 4,060,088 | 11/1977 | Morrison, Jr. et al. | 128/303.17 |
| 4,325,362 | 4/1982 | Ouchi et al. | 600/158 |
| 4,402,310 | 9/1983 | Kimura | 600/158 |
| 4,425,115 | 1/1984 | Wuchinich | 604/22 |
| 4,428,748 | 1/1984 | Peyman et al. | 604/22 |
| 4,781,175 | 11/1988 | McGreevy et al. | 128/303.17 |
| 4,804,364 | 2/1989 | Dieras et al. | |
| 4,808,153 | 2/1989 | Parisi | 604/22 |
| 4,816,018 | 3/1989 | Parisi | 604/22 |
| 4,867,141 | 9/1989 | Nakada et al. | 604/22 |
| 4,901,719 | 2/1990 | Trenconsky et al. | 606/49 |
| 4,901,720 | 2/1990 | Bertrand | 606/40 |
| 4,936,281 | 6/1990 | Stasz | 604/22 |
| 5,009,656 | 4/1991 | Reimels | 606/48 |
| 5,242,385 | 9/1993 | Strukel | 604/22 |
| 5,312,329 | 5/1994 | Beaty et al. | 604/22 |
| 5,334,183 | 8/1994 | Wuchinich | 604/22 |

FOREIGN PATENT DOCUMENTS

| | | |
|---|---|---|
| 0514651 | 11/1992 | European Pat. Off. . |
| 3710489 | 11/1987 | Germany . |
| 8914513 | 3/1990 | Germany . |
| 9104559 | 9/1992 | Germany . |
| 2101893 | 1/1983 | United Kingdom ............... 606/50 |

OTHER PUBLICATIONS

Söring Medizintechnik GmbH, "ARCO–T® Inert Gas Coagulator", 1992, (first published Aug. 1991).

*Primary Examiner*—Mark Bockelman
*Attorney, Agent, or Firm*—Fitzpatrick, Cella, Harper & Scinto

[57] ABSTRACT

A diathermic hand-held instrument (1) and a detachable endoscopic probe (101) for use in surgical operations, particularly in laprascopic ultrasonic dissections during which surgery-related hemorrhaging must be stopped, e.g., by means of inert gas welding the blood vessels. The endoscopic probe (101) of the present invention provides for both coagulation and dissection in one tool. In particular, a sonotrode (8) that receives a gas supply line (19) and a suction line (6) is embodied to be electrically conductive. The endoscopic probe (101) also may be attached to alternative hand-held instruments.

17 Claims, 2 Drawing Sheets

DIATHERMIC HAND-HELD INSTRUMENT WITH AN ENDOSCOPIC PROBE

This application is a continuation of application Ser. No. 08/222,301 filed Apr. 4, 1994, now abandoned.

BACKGROUND OF THE INVENTION

1. Field of the Invention

The present invention relates to a diathermic hand-held instrument for use in surgical procedures. With the aid of instruments of this type, cancerous tumors are surgically removed in a known manner using ultrasonic oscillations. These ultrasonic oscillations are generated in a handle region of the hand-held instrument and transmitted to the tip of a probe of the instrument which resects the cancerous tumor tissue. A rinsing agent supply line and a suction line are provided in fluid communication with the tip region of the probe and facing the operating site.

2. Related Background Art

Hand-held instruments of this type have proven useful in the surgical removal of cancerous tumors. Such hand-held instruments act as ultrasonic tissue crushers. The functioning principle is that high-frequency, longitudinal oscillations (approximately 24 Khz) are generated and transmitted through a probe by transducers disposed in the handle or proximate region of the hand-held instrument. A distal tip of the probe executes longitudinal oscillations that destroy cancer tissue, which is considerably more sensitive to mechanical stress than healthy tissue. By means of the oscillations in the region of the probe tip, tumor tissue that comes into contact with the tip is disintegrated. With the aid of a rinsing fluid supplied via a rinsing agent supply line, such disintegrated tissue is suctioned off via a suction line.

Because of damage to associated blood vessels, severe hemorrhaging can occur during this type of surgical procedure. Such hemorrhaging must be stopped as quickly as possible. Typically, hemorrhaging of this kind is stopped with the aid of additional devices, such as clamps, resistance-wire electrodes, and the like.

One example of a hand-held instrument with a built-in rinsing agent supply line and an integrated suction line is described in German Utility Patent DE-GM No. 89 14 513. However, when severe hemorrhaging occurs during operations executed with this instrument, it has been found that the above-described additional tools still are needed.

Conventionally, hemorrhaging is stopped within an open operating site by a known coagulating technique, wherein capillary vessels are welded together with the aid of a micro-electric, inert-gas welding tool. One example of a tool of this type is described in detail in German Published, Non-Examined Patent Application DE-OS 37 10 489 (equivalent to U.S. Pat. No. 4,781,175). In that tool, electrical energy is conducted in electric arcs to tissue in a living organism through which blood flows to effect electrosurgical coagulation. This tool also provides for removal of blood from the surface of a tissue by conducting a continuous laminar jet of ionizable gas. In this manner, a scab or eschar with predetermined properties is produced by conducting electrical energy in electrical arcs.

As shown in U.S. Pat. No. 4,781,175, one pen-like, hand-held instrument can be manipulated by the surgeon during the coagulation procedure. Such an instrument comprises a nozzle for generating a gas jet, and a structure including an electrode disposed in the gas jet for transmitting electrical energy, and a cord connects the hand-held instrument to both a gas supply device and to an electrical generator. The cord embodies a plurality of gas-conducting hollow chambers extending over its length and disposed around an electrical conductor. In other words, all of these chambers extend parallel to the electrical conductor.

Such a pen-like, hand-held instrument also includes a handle that is connected to the cord, a nozzle- and electrode-holding device to which the nozzle and the electrode are connected in integral fashion, and a coupling device. The coupling device is connected to the handle to allow detachable connections of the nozzle- and electrode-holding device with the hand-held instrument. In addition, the coupling device both electrically connects the electrode to the electrical conductor of the cord and also conducts gas from the gas conducting conduit into the nozzle.

Another known micro-welding device of this same type is described in German Utility Patent No. 91 04 559, which illustrates a structure simplified with respect to the tool as described in DE-OS 37 10 489.

Both known systems perform an inert gas coagulation utilizing a central electrode as the electrical conductor that is disposed in the rinsing gas current for supplying the electrical energy needed to ionize gas at the exit point of the device. Because that central electrode inside the gas current chamber is not fixed with respect to the chamber wall over substantial portions of its length, a number of distinct, undefined changes in electrode location occur during use. Further, electrode bending vibrations occur depending on the mechanical strength of the conductor. Hence, the shape of the gas current cross-section constantly changes, and this causes turbulence in the gas current.

There also is a feedback of such turbulence to the central electrode, which is capable of oscillating. The feedback intensifies such oscillations, and causes a "buildup" of turbulence which generates short-term resonances, which are noticed as singing or crackling noises and often occur with these methods. Electrical instabilities within an initiated plasma jet also may be caused by standing waves due to such resonances, and such instabilities cause a layering of the plasma into light and dark regions.

As a result of such method-related, inherent turbulences, conventional micro-welding devices have the further drawback that atmospheric oxygen will become entrained in the rinsing gas current, whereby an oxidation will take place on the tissue surface to be coagulated. Such an oxidation is intended to be avoided with the selection of an inert gas as the rinsing gas, but a discoloration of the plasma jet is a characteristic that indicates an unwanted entrainment of air.

Also, as a result of thermodynamic interactions (e.g., differences in density and temperature), generation of a plasma jet through ionization of a gas current that is initiated at its center will cause an expansion of the plasma jet. Such a jet then will attain a final effective cross-section of up to several square millimeters on the tissue surface to be coagulated. Expansion of the plasma jet is further increased by electromagnetic rotational fields formed inside the highly-ionized core region. Hence, very precise operation of the device, as demanded by microsurgery and neurosurgery, for example, is not possible.

A tubular sonotrode device, without any provision for suction line or rinsing agent function, is illustrated by MORRISON, ET AL. (U.S. Pat. No. 4,060,088).

OBJECT AND SUMMARY OF THE INVENTION

Therefore, an object of the present invention is to provide a diathermic hand-held instrument which not only safely and reliably resects and removes cancerous tumor tissue from an operating site, but also which is capable of stopping hemorrhages that occur during such a procedure, by welding blood vessels together.

These and other objects and features are provided by the present invention, in which a gas supply is disposed in a central region of the hand-held instrument, and an endoscopic probe including an electrically conductive sonotrode serves both as a gas supply line and as a suction conduit.

In one embodiment, an endoscopic probe is provided with a coupling device that provides a gas-tight and electrically insulated connection between the endoscopic probe and a hand-held instrument. The endoscopic probe includes multiple layers, including an electrically conductive material and at least one insulating covering to protect the user of the probe and the patient.

Exemplary embodiments of the invention are described in further detail in conjunction with the drawings in the following description.

DETAILED DESCRIPTION OF THE PREFERRED EMBODIMENTS

Figure 1:
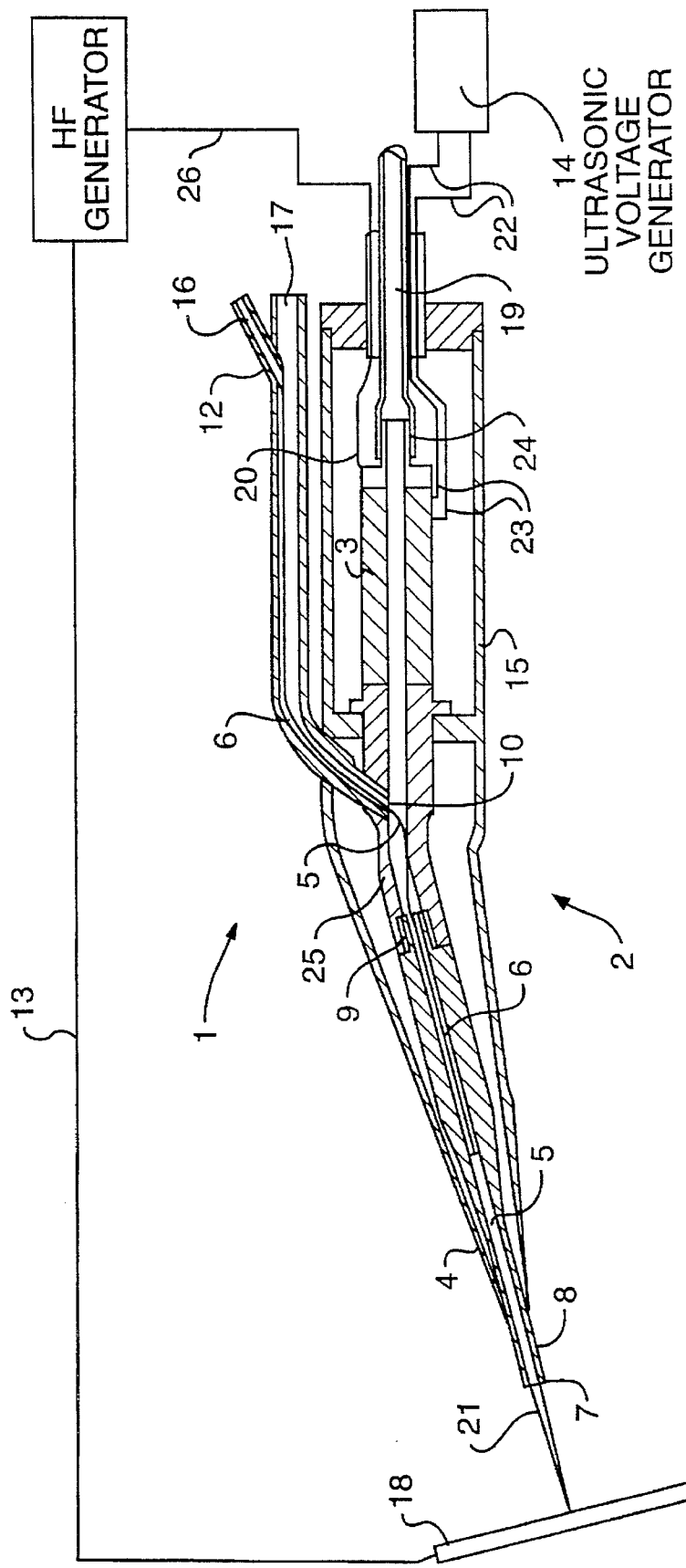
FIG. 1 is a longitudinal section through a diathermic hand-held instrument of the present invention.

As shown in FIG. 1, a hand-held diathermic instrument 1 comprises a gripping sleeve 15 provided with a grip area 2, transducers 3 for generating ultrasonic oscillations, and a connector 25, which supports a sonotrode 8 in a sonotrode receptacle 9. Instrument 1 also comprises a suction line 6, a gas line 19, and electric driving signal supply lines 22 and 26.

Sonotrode 8 is preferably made of titanium. However, other conductive materials suitable for transmitting ultrasonic oscillationals also may be used. A rinsing agent supply line 5 is provided in a portion of a hollow core 6' of sonotrode 8, which is illustrated as a pipe. Rinsing agent supply line 5 is guided through connector 25 to a discharge region 10 thereof, and then through suction line 6. Rinsing agent supply line 5 exits suction line 6 through a branch part 12, and ends at a connecting port 16. Connecting port 16 may be connected to a conventional rinsing agent supply (not shown). The rinsing agent supply line 5 discharge terminates interior to the tip 7 of sonotrode 8 to provide an unobstructed passage for gas flow at an exit opening 115.

Liquids and tissue residue can be suctioned away from the operating site via suction line means including suction line 6. Specifically, hollow core 6' of sonotrode 8 and suction line 6 are arranged in fluid communication through discharge region 10 of connector 25. Suction line 6 terminates at connection 17, to allow connection to a conventional external suction line (not shown). The surgeon can turn the rinsing or suction devices on or off by means of a conventional switch (not shown), which is preferably operated with the foot.

A gas supply line 19 may be secured to an adapter 24 of hand-held instrument 1, to provide a supply of inert gas through a fluid-tight hollow central core 27 of transducers 3 and connector 25, to the hollow core 6' of sonotrode 8. An electrical connecting line 26 from an HF generator 11 to a high-frequency connector 20 also is provided in hand-held instrument 1, to provide a driving signal for performing an inert gas coagulation or a micro-welding function. The electrical connecting line 26 also can be operated by the surgeon by means of a conventional switch (not shown).

Should inert gas coagulation become necessary during an ultrasonic resection, the gas supply line 19 first is opened. Subsequently, a plasma jet 21 sufficient for coagulation is triggered by activating the HF voltage, as needed. To assure a reliable "start" of the plasma jet, a good electrical contact must be provided between the patient and the opposite pole plate 18, which also is connected to the high-frequency generator 11 via an electric line 13.

After an inert gas coagulation procedure has been completed, ultrasonic resection can be continued by means of a simple switchover. An ultrasonic oscillation generator 14 is connected to ultrasonic connectors 23 of transducer 3 via electric signal supply lines 22.

Figure 2:
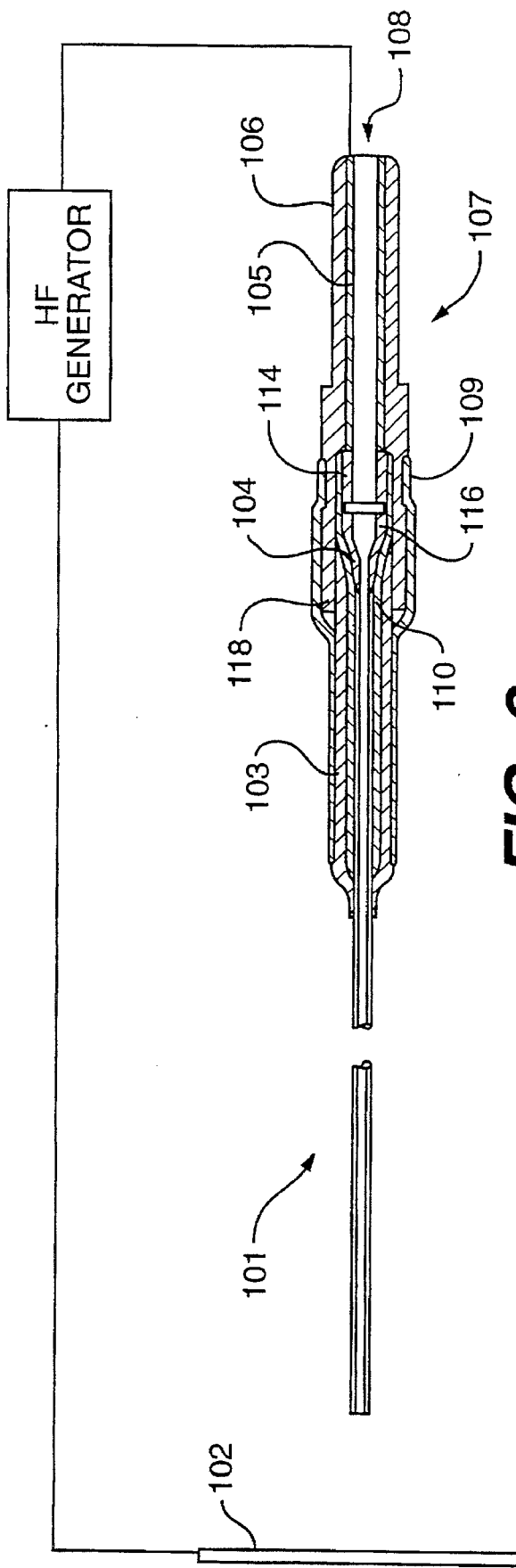
FIG. 2 is a longitudinal section through an embodiment of an endoscopic probe of the present invention.
Figure 3:
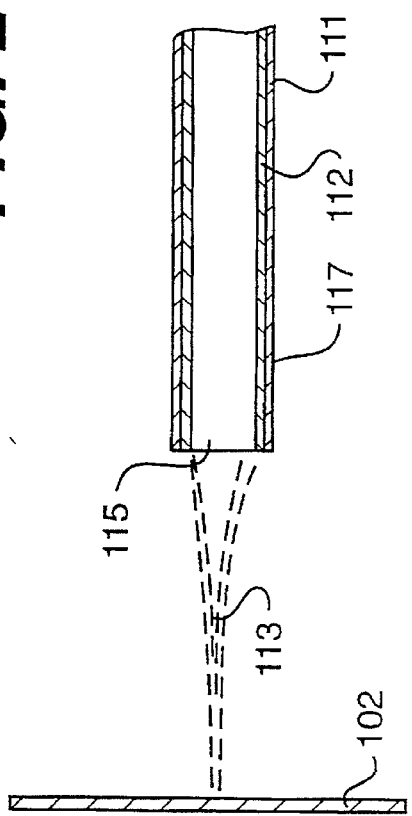
FIG. 3 is an enlarged representation of the exit region of the endoscopic probe of FIG. 2.

FIGS. 2 and 3 illustrate in detail one embodiment of a detachable endoscopic probe of the present invention. Endoscopic probe 101 generally comprises a flexible tube 120, a probe head 106 and a coupling 107. Endoscopic probe 101 may be connected, e.g., to connector 25 of hand-held instrument 1, by inserting coupling 107 into sonotrode receptacle 9.

Flexible tube 120 comprises an inner tube 112 composed of an electrically conductive material, such as a spiral element produced in the manner of a Bowden cable, a metallic tissue, an interlaced metallic material, or the like. A protective hose 111 insulates electrically conductive inner tube 112, and provides a gas-tight and high-frequency-tight outer layer. Protective hose 111 can be composed of any material suitable for this purpose, and preferably is composed of polytetraflouroethylene (PTFE), or the like.

An exit opening 115 at the distal end of a tip 7 to the flexible tube 120 can be covered with a heat-resistant material, preferably ceramic 117, to prevent melting or damage to protective hose 111 due to high temperatures at the exit opening 115. The ceramic in turn helps to prevent contamination of the operating area.

A contact connection 104 is provided at the other end of flexible tube 120, i.e., at the proximal end, or adjacent to the hand-held instrument. Contact connection 104 electrically connects inner tube 111 of flexible tube 120 with probe head 116, by means of welding, soldering, or the like. Probe head 116 has an interior thread 114 for providing a gas-tight and HF-tight transition from adapter 106 to probe head 116. As noted above, adapter 106 is insertable into a corresponding opening of a hand-held instrument, e.g., into a sonotrode receptacle 9 of hand-held instrument 1 (see FIG. 1). In this case, a tight connection that does not interrupt electrical contact to the hand-held instrument must, of course, be assured. Such a connection can be achieved by conventional means of clamping, pressing, screws, or the like.

A gas flow 108 is conducted through a supply tube 105 of coupling 107. To ensure that gas does not escape at an undesired point, and to ensure that high-frequency blowouts do not occur, the connection region may be insulated with multiple layers of insulation, and preferably layers of shrink-down or heat-shrinkable plastic tubing.

After the probe tube 112 and the probe head 116 are connected, this region preferably is covered with insulation 110. As shown in FIG. 2, insulation 110 completely covers the probe head 116 and seals the interior region of tubular extension 118 of coupling 107. A second seal in the interior region of tubular extension 118 is achieved by additional insulation 103.

To prevent screw connection 114 from vibrating loose during use of hand-held instrument 1, and causing a leak in this area that would be dangerous to the doctor and patient, the entire connection area preferably is protected by a shrinkdown insulating plastic tubing section 109.

The adapter 106 of the endoscopic probe 101 preferably is embodied such that it can be connected not only to a hand-held instrument for a micro-electric or inert-gas welding tool, as shown in FIG. 1, but also connected to pieces of different manipulators, or optical tools. When endoscopic probe 101 of the present invention is used for performing a coagulation operation, after the micro-electric, inert-gas welding tool is connected to the hand-held instrument 1, the exit opening 115 for forming the plasma jet 21 of endoscopic probe 101 is directed to the tissue to be coagulated. After the gas supply is opened, a high-frequency A.C. voltage is applied that triggers the electric arc required for coagulation. To assure a reliable "start" of the electric arc, a good electrical contact must be provided between the opposite pole plate 18 and the patient. The exit opening 115 of the tip 7 of endoscopic probe 101 preferably has a diameter smaller than the diameter of gas line 19, and may be provided with a ceramic covering 117, so that the plastic does not melt because of possible high temperatures and drip onto the operating site, thereby contaminating it.

All connections to the hand-held instrument 1, such as fluid supply lines or hoses, and electrical cables or lines, preferably are detachable, so that the hand-held instrument 1 and endoscopic probe 101 of the present invention can be sterilized repeatedly using high pressure, saturated steam when each operation is finished.

While preferred embodiments of the invention have been shown and described, the invention is not limited thereto, and is to be defined by the scope of the appended claims.

What is claimed is:

1. A diathermic handpiece for use in medical procedures for conducting ultrasonic dissection and for welding blood vessels in a subject connected to a pole plate (18), said handpiece (1) comprising: a sonotrode (8), the sonotrode (8) being coupled to a sleeve of said handpiece (1), the sleeve having disposed therein a transducer (3) for supplying ultrasonic oscillations to the sonotrode (8), and (ii) a suction drain (6) in fluid communication with the sonotrode (8) for removal of fluids therethrough, said handpiece (1) further comprising:

gas supply means coupled to the sonotrode (8) for supplying inert gas to the sonotrode (8), said gas supply means being disposed in a center part of the sleeve; and a rinsing agent supply hose (5) disposed in an inner part of the sonotrode (8) and the suction drain (6), and ending shortly before a tip (7) of the sonotrode (8), wherein the sonotrode (8) is composed of electrically conductive material, and has (a) an exit opening disposed at the tip (7) and (b) an inert gas passage (6') in fluid communication with said gas supply means, said inert gas passage (6') extending through the sonotrode (8) to the exit opening through which the inert gas supplied by the gas supply means flows, and wherein, upon application of inert gas from a gas supply to said gas supply means and application of high-frequency energy to the sonotrode (8) and the pole plate (18), a plasma beam for inert gas coagulation is generated between the sonotrode (8) and the subject.

2. A handpiece according to claim 1, wherein the exit opening of the tip (7) of the sonotrode (8) has a smaller inside diameter than the inside diameter of the gas supply means.

3. A handpiece according to claim 2, further comprising a connector (25) for connecting the transducer (3) and the sonotrode (8), wherein each of the transducer (3) and said connector (25) have hollow portions (27) therethrough for supply of the inert gas to the sonotrode (8).

4. A handpiece according to claim 1, wherein the tip (7) of the sonotrode (8) comprises a ceramic covering (117).

5. A handpiece according to claim 4, further comprising a connector (25) for connecting the transducer (3) and the sonotrode (8), wherein each of the transducer (3) and said connector (25) have hollow portions (27) therethrough for supply of the inert gas to the sonotrode (8).

6. A handpiece according to claim 1, wherein an inert gas supply and a suction supply are detachably connected to said handpiece (1).

7. A handpiece according to claim 1, further comprising a connector (25) for connecting the transducer (3) and the sonotrode (8), wherein each of the transducer (3) and said connector (25) have hollow portions (27) therethrough for supply of the inert gas to the sonotrode (8).

8. A diathermic handpiece for use in medical procedures for conducting ultrasonic dissection and for welding blood vessels in a subject electrically connected to a pole plate (18), the pole plate (18) being electrically connected to a high-frequency generator, said handpiece (1) comprising:

a sonotrode (8);

a transducer (3), coupled to said sonotrode (8), for supplying ultrasonic oscillations to said sonotrode (8);

a suction drain (6) in fluid communication with said sonotrode (8) for removal of fluids therethrough;

gas supply means coupled to said sonotrode (8) for supplying inert gas to said sonotrode (8), said gas supply means being disposed within said handpiece (1);

a rinsing agent supply hose (5) disposed in an inner part of said sonotrode (8) and said suction drain (6), and ending shortly before a tip (7) of said sonotrode (8); and electrical connecting means for electrically connecting said sonotrode (8) with the high-frequency generator, wherein said sonotrode (8) is composed of electrically conductive material, and has (a) an exit opening disposed at the tip (7) and (b) an inert gas passage (6') in fluid communication with said gas supply means, said inert gas passage (6') extending through said sonotrode (8) to the exit opening through which the inert gas supplied by the gas supply means flows, and wherein, upon application of inert gas from a gas supply to said gas supply means and application of high-frequency energy from the high-frequency generator to (i) said sonotrode (8) via said electrical connecting means, and (ii) the pole plate (18), a plasma beam for inert gas coagulation is generated between said sonotrode (8) and the subject.

9. A handpiece according to claim 8, further comprising a connector for connecting said transducer and said sonotrode, wherein each of said connector and said transducer have hollow portions therethrough for supply of the inert gas to said sonotrode.

10. A handpiece according to claim 8, wherein said tip end of said sonotrode comprises a ceramic covering.

11. A diathermic handpiece apparatus for use on a subject, said apparatus being adapted for use with (a) a high-frequency generator for supplying a high-frequency driving signal, the subject being electrically connected to the high-frequency generator, and (b) a gas supply for supplying inert gas to said apparatus, said apparatus comprising:

a sonotrode for performing ultrasonic dissection;

a transducer, coupled to said sonotrode, for supplying ultrasonic oscillations to said sonotrode;

suction means, for removing fluids from said sonotrode, said suction means comprising a suction drain in fluid communication with said sonotrode for removal of fluids therethrough;

rinsing means, for supplying a rinsing agent to said sonotrode, said rinsing means comprising a rinsing agent supply hose that is disposed in an inner part of said sonotrode and said suction drain, and ends shortly before a tip end of said sonotrode; and gas supply means within said handpiece apparatus for supplying inert gas to said sonotrode, said sonotrode being composed of electrically conductive material and having (a) an exit opening disposed at the tip end of said sonotrode and (b) an inert gas passage in fluid communication between said gas supply means and said exit opening, wherein inert gas supplied by said gas supply means will flow through said exit opening; and electrical connection means for electrically connecting said sonotrode with the high-frequency generator, wherein upon application of inert gas from the gas supply to said gas supply means and application of the high-frequency driving signal from the high-frequency generator (i) to said sonotrode via said electrical connection means and (ii) to the subject, a plasma jet for inert gas coagulation is generated between said sonotrode and the subject.

12. An apparatus according to claim 11, further comprising a connector for connecting said transducer and said sonotrode, wherein each of said connector and said transducer have hollow portions therethrough for supply of the inert gas to said sonotrode.

13. A system for operating on a subject, said system being for use with a gas supply for supplying inert gas, said system comprising:

a high-frequency signal generator for providing a high-frequency driving signal across first and second electrical connections, said first electrical connection including a pole plate for forming an electrical connection with the subject;

a handpiece comprising (a) a sonotrode for performing ultrasonic dissection, (b) a transducer, coupled to said sonotrode, for supplying ultrasonic oscillations to said sonotrode, (c) gas supply means coupled to said sonotrode for supplying inert gas to said sonotrode, said sonotrode being composed of electrically conductive material and having (i) an exit opening disposed at a tip end of said sonotrode and (ii) an inert gas passage in fluid communication between said gas supply means and said exit opening, wherein inert gas supplied by said gas supply means will flow through said exit opening, (d) electrical connection means for electrically connecting said sonotrode with said second electrical connection of said high-frequency generator, (e) a suction drain that is in fluid communication with said sonotrode for removal of fluids through said sonotrode, and (f) a rinsing agent supply hose disposed within an inner part of said sonotrode and within said suction drain, and said hose ends shortly before the tip end of said sonotrode;

wherein upon application of inert gas from the gas supply to said gas supply means and application of the high-frequency driving signal from said high-frequency generator (i) to said sonotrode via said electrical connection means and (ii) to the subject, a plasma jet for inert gas coagulation is generated between said sonotrode and the subject.

14. A system according to claim 13, further comprising a connector for connecting said transducer and said sonotrode, wherein each of said connector and said transducer have hollow portions therethrough for supply of the inert gas to said sonotrode.

15. A system according to claim 13, further comprising the inert gas supply.

16. A system for operating on a subject, said system being for use with a gas supply for supplying inert gas, said system comprising:

a high-frequency signal generator for providing a high-frequency driving signal across first and second electrical connections, said first electrical connection including a pole plate for forming an electrical connection with the subject;

a handpiece comprising (a) a sonotrode for performing ultrasonic dissection, (b) a transducer, coupled to said sonotrode, for supplying ultrasonic oscillations to said sonotrode, (c) gas supply means coupled to said sonotrode for supplying inert gas to said sonotrode, said sonotrode being composed of electrically conductive material and having (i) an exit opening disposed at a tip end of said sonotrode and (ii) an inert gas passage in fluid communication between said gas supply means and said exit opening, wherein inert gas supplied by said gas supply means will flow through said exit opening, (d) electrical connection means for electrically connecting said sonotrode with said second electrical connection of said high-frequency generator, (e) a suction drain for removal of fluids through said sonotrode, and (f) a rinsing agent supply for supplying fluids;

wherein upon application of inert gas from the gas supply to said gas supply means and application of the high-frequency driving signal from said high-frequency generator (i) to said sonotrode via said electrical connection means and (ii) to the subject, a plasma jet for inert gas coagulation is generated between said sonotrode and the subject;

wherein the tip end of said sonotrode comprises a ceramic covering.

17. A diathermic handpiece apparatus for use on a subject, said apparatus being adapted for use with (a) a high-frequency generator for supplying a high-frequency driving signal, the subject being electrically connected to the high-frequency generator, and (b) a gas supply for supplying inert gas to said apparatus, said apparatus comprising:

a sonotrode for performing ultrasonic dissection;

a transducer, coupled to said sonotrode, for supplying ultrasonic oscillations to said sonotrode;

suction means for removing fluids from said sonotrode;

rinsing means for supplying a rinsing agent to said sonotrode; and gas supply means within said handpiece apparatus for supplying inert gas to said sonotrode, said sonotrode being composed of electrically conductive material and having (a) an exit opening disposed at the tip end of said sonotrode and (b) an inert gas passage in fluid communication between said gas supply means and said exit opening, wherein inert gas supplied by said gas supply means will flow through said exit opening; and electrical connection means for electrically connecting said sonotrode with the high-frequency generator, wherein upon application of inert gas from the gas supply to said gas supply means and application of the high-frequency driving signal from the high-frequency generator (i) to said sonotrode via said electrical connection means and (ii) to the subject, a plasma jet for inert gas coagulation is generated between said sonotrode and the subject;

wherein the tip end of said sonotrode comprises a ceramic covering.

* * * * *